US010194914B2

(12) United States Patent
Mooney (10) Patent No.: US 10,194,914 B2
(45) Date of Patent: Feb. 5, 2019

(54) ANASTOMOSIS DEVICES (71) Applicant: W. L. Gore & Associates, Inc., Newark, DE (US)

(72) Inventor: Nathan K. Mooney, Elkton, MD (US)

(73) Assignee: W. L. Gore & Associates, Inc., Newark, DE (US)

( * ) Notice: Subject to any disclaimer, the term of this patent is extended or adjusted under 35 U.S.C. 154(b) by 237 days.

(21) Appl. No.: 14/818,800

(22) Filed: Aug. 5, 2015

(65) Prior Publication Data
US 2016/0045199 A1 Feb. 18, 2016

Related U.S. Application Data (60) Provisional application No. 62/037,363, filed on Aug. 14, 2014.

(51) Int. Cl.
*A61B 17/11* (2006.01)
*A61B 19/00* (2006.01)
*A61B 17/00* (2006.01)

(52) U.S. Cl.
CPC ........ *A61B 17/11* (2013.01); *A61B 17/00234* (2013.01); *A61B 19/54* (2013.01); *A61B 2017/00243* (2013.01); *A61B 2017/1107* (2013.01); *A61B 2017/1132* (2013.01); *A61B 2017/1139* (2013.01); *A61B 2019/5466* (2013.01)

(58) Field of Classification Search
CPC ............ A61B 17/11; A61B 2017/1107; A61B 2017/1132; A61B 2017/1139
USPC .................................. 606/153–156, 213–216
See application file for complete search history.

(56) References Cited

U.S. PATENT DOCUMENTS

| | | | |
|---|---|---|---|
| 3,174,851 A | 3/1965 | Buehler et al. | |
| 3,351,463 A | 11/1967 | Rozner et al. | |
| 3,753,700 A | 8/1973 | Harrison et al. | |
| 6,451,048 B1 * | 9/2002 | Berg ....................... A61F 2/064 | |
| | | | 606/153 |
| 6,616,675 B1 * | 9/2003 | Evard .................. A61B 1/3137 |
| | | | 606/153 |
| 8,523,800 B2 | 9/2013 | Brenneman et al. | |
| 2005/0049675 A1 | 3/2005 | Wallace | |
| 2005/0070934 A1 | 3/2005 | Tanaka | |
| 2011/0054381 A1 | 3/2011 | Van Dam et al. | |
| 2011/0118765 A1 | 5/2011 | Aguirre | |

FOREIGN PATENT DOCUMENTS

WO WO-1997027898 A1 8/1997

* cited by examiner

*Primary Examiner* — Kathleen Holwerda (57) ABSTRACT

An implantable medical device for connecting tissue layers, such as connecting tubular tissues to create an anastomosis, includes a single elongate member and a covering material. The devices provided may also be used for other purposes including, but not limited to, partially or fully occluding openings in tissue, temporarily or permanently holding generally planar layers of tissue together, aneurysm repair, and the like.

25 Claims, 8 Drawing Sheets

ANASTOMOSIS DEVICES

FIELD

This document relates to implantable medical devices, and more particularly, to implantable devices for connecting tubular tissues to create an anastomosis.

BACKGROUND

An anastomosis is a surgical connection between two tubular tissue structures, such as blood vessels or intestines. For example, when a portion of an intestine is resected, the resulting two ends can be sewn or stapled together (anastomosed), using an intestinal anastornosis procedure. This procedure can restore intestinal continuity after the resection of a bowel portion, or to bypass a portion of unresectable diseased bowel.

Portions of bowel may be resected for various reasons including, but not limited to: bowel gangrene due to vascular compromise caused by mesenteric vascular disease, prolonged intestinal obstruction, intussusceptions, malignancy conditions, benign conditions (e.g., intestinal polyps, intussusception, roundworm infestation with intestinal obstruction), infections (e.g., tuberculosis complicated with stricture or perforation), traumatic perforations, inflammatory bowel disease, ulcerative colitis, and Crohn's disease. Bypass of unresectable diseased bowel may be needed in situations including, but not limited to: locally advanced tumors causing luminal obstruction, metastatic disease causing intestinal obstruction, poor general condition or condition that prevents major resection, and various pediatric conditions.

A circulatory anastomosis is a connection (an anastomosis) between two blood vessels, such as between arteries (arterio-arterial anastomosis), between veins (veno-venous anastomosis), or between an artery and a vein (arterio-venous anastomosis).

Anastomoses can be created in various manners including, but not limited to: end-to-end, end-to-side, and side-to-side anastomoses. Often, suturing is used to create such anastomoses.

SUMMARY

This document provides implantable medical devices. For example, this document provides implantable devices for connecting tissue layers, including connecting tubular tissues to create an anastomosis. The devices provided may also be used for other purposes including, but not limited to, partially or fully occluding openings in tissue, temporarily or permanently holding generally planar layers of tissue together, aneurysm repair, and the like.

One embodiment of the invention relates to a medical device for creating an anastomosis between a first body conduit and a second body conduit. The medical device includes (1) a frame that includes an elongate member and (2) a covering material. The elongate member defines (1) a first apposition portion configured to conform to a geometry of a first tissue surface of the first body conduit and to provide an apposition force against the first tissue surface, (2) a second apposition portion configured to conform to a geometry of a second tissue surface of the second body conduit and to provide an apposition force against the second tissue surface, and (3) a central portion disposed between the first apposition portion and the second apposition portion, the central portion defining a lumen therethrough. The covering material may be disposed on at least a portion of the central portion. Additionally, the covering material is configured to allow material to flow through the lumen and between the first body conduit and the second body conduit. The elongate member is wound in a pattern where (1) the elongate member defines a first feature, (2) the elongate member traverses the central portion, (3) the elongate member defines a second feature, (4) the elongate member traverses the central portion and (5) the elongate member repeats the pattern such that a plurality of first features and a plurality of second features is formed.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

DETAILED DESCRIPTION

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Figure 1A:
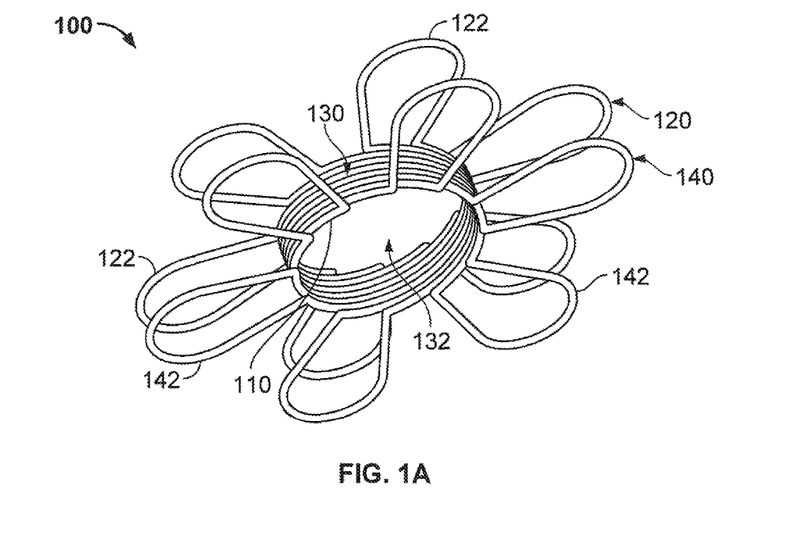
FIG. 1A is a perspective view of a wire frame of an example anastomosis device in a contracted configuration.
Figure 1B:
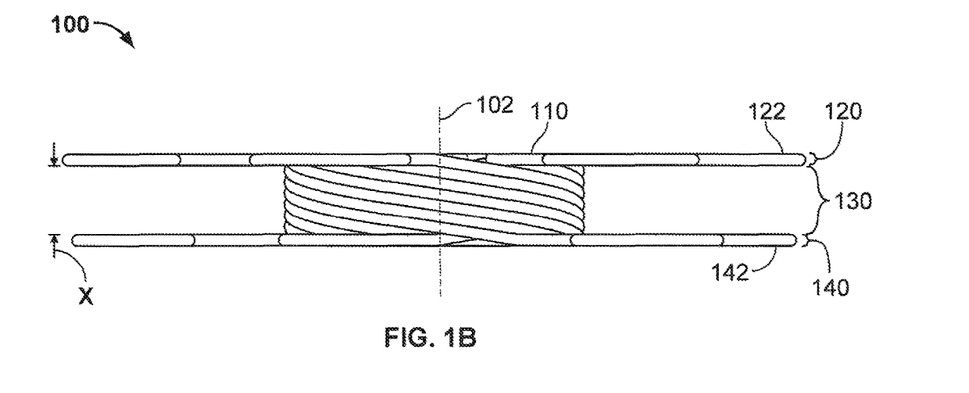
FIG. 1B is a side view of the wire frame of FIG. 1A in a contracted configuration.
Figure 2:
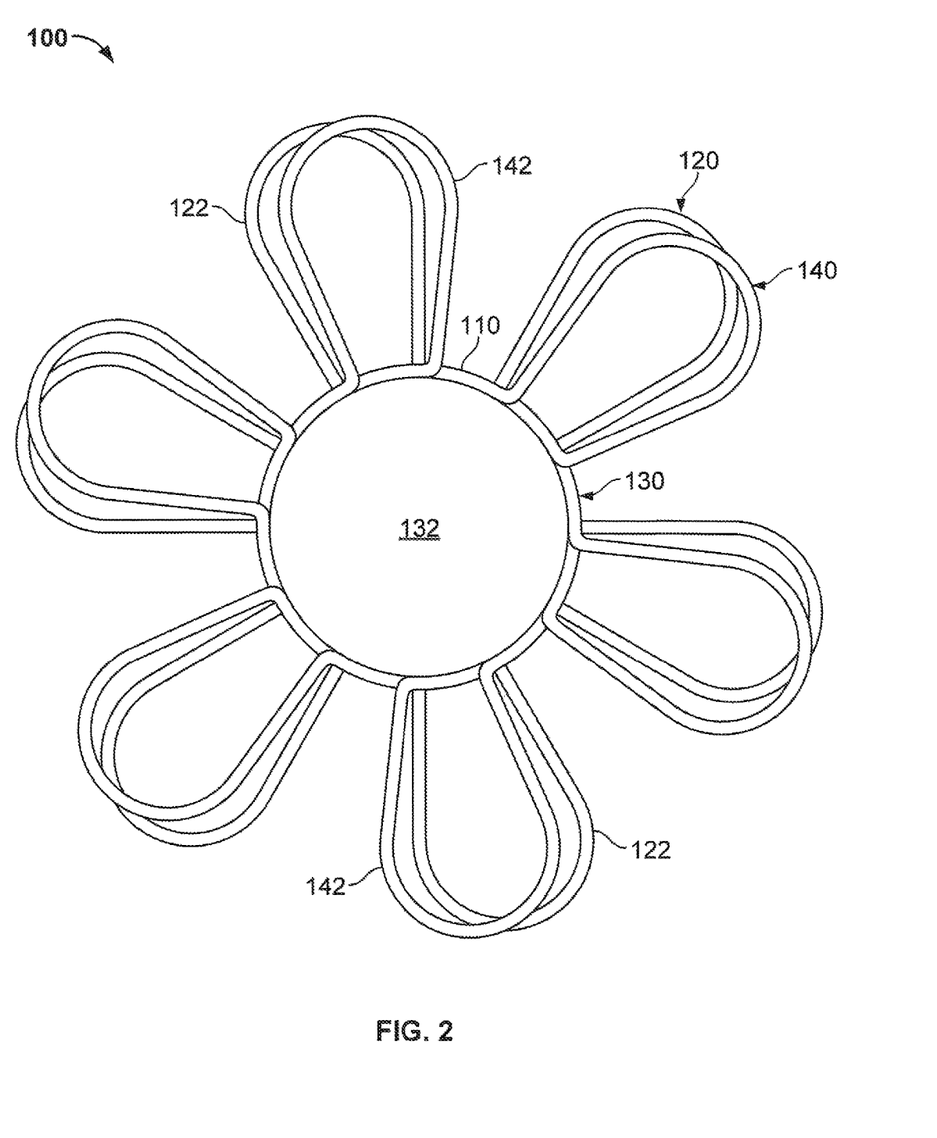
FIG. 2 is an end view of the wire frame of FIG. 1A.

In reference to FIGS. 1A, 1B, and 2, a frame 100 of an example anastomosis device includes an elongate member 110. The elongate member 110 is configured to form a first apposition portion 120, a central portion 130, and a second apposition portion 140. The central portion 130 is disposed between the first apposition portion 120 and the second apposition portion 140. In some embodiments, the central portion 130 defines a lumen 132 that extends between the first apposition portion 120 and the second apposition portion 140. The frame 100 is shown in a contracted configuration. In some embodiments, the contracted configuration is the configuration that the frame 100 naturally exhibits in the absence of external forces acting upon the frame 100.

The first and second apposition portions 120 and 140 are configured to engage one or more layers of tissue therebetween, and to provide apposition forces against the tissue surfaces. The apposition forces provided by the first and second apposition portions 120 and 140 can provide attachment of the frame 100 to the tissue and migration resistance such that the frame 100 can reliably remain positioned at a target site in a patient as desired. In some embodiments, each of the first and second apposition portions 120 and 140 are configured to form, in a general sense, discs that contact tissue surfaces.

In some embodiments, the lumen 132 provides an anastomosis passageway or tunnel through which materials can pass. In some embodiments, the frame 100 is configured to be a sealing device and no lumen 132 is provided, or the lumen 132 is occluded by other material such as a covering material.

In some embodiments, the elongate member 110 comprises a single continuous wire. As will be described further below in reference to FIGS. 6A and 6B, the single continuous wire can be bent using a mandrel to form the frame 100.

The elongate member 110 can comprise a variety of materials. The elongate member 110 may be elastomeric, metallic, a spring wire, a shape memory alloy wire, a super-elastic alloy wire, or combinations and sub-combinations thereof, to name a few general examples. In fact, any type of elongate member 110 that is suitably biocompatible, flexible, and resilient can generally be used for the anastomosis devices provided herein. For example, the elongate member 110 can comprise nitinol (NiTi), L605 steel, stainless steel, polymeric materials, or any other appropriate biocompatible material, including combinations and sub-combinations of materials. In some embodiments, bioresorbable or bioabsorbable materials may be used, including, for example, a bioresorbable or bioabsorbable polymer. In some such embodiments, the elongate member 110, or portions thereof, may eventually dissolve. In some embodiments, the elongate member 110 is fully or partially coated to facilitate a biological reaction, such as, but not limited to, endothelial cell attachment, endothelial cell migration, endothelial cell proliferation, and resistance to or promotion of thrombosis.

It should be clear that suitable materials for the elongate member 110 include a variety of metallic shape memory materials and super-elastic alloys. Shape memory refers to the ability of a material to revert to an originally memorized shape after plastic deformation by heating above a critical temperature. Super-elasticity refers to the ability of a material to deform under strain to a very large degree, without having this deformation become permanent. For example, the super-elastic materials included in the frames of some anastomosis device embodiments provided herein are able to withstand a significant amount of bending and flexing and then return to the frame's original form without deformation. Some metallic shape memory materials used in the anastomosis devices are described in U.S. Pat. Nos. 3,174,851; 3,351,463; and 3,753,700, all of which are hereby incorporated by reference in their entireties. In some embodiments, suitable shape memory and super-elastic materials include various stainless steels which have been physically, chemically, and otherwise treated to produce high springiness, metal alloys such as cobalt chrome alloys (e.g., ELGILOY™), platinum/tungsten alloys, and the NiTi alloys.

The super-elastic properties of NiTi make it a suitable material for the elongate member 110 of some embodiments of the anastomosis devices provided herein. NiTi elongate members 110 can be heat-set into a desired shape such that the NiTi elongate member 110 will tend to self-expand from a low-profile delivery configuration into the desired shape when deployed from a delivery sheath to a target site within a body.

In some embodiments, the elongate member 110 can be treated in various ways to increase the radiopacity of the elongate member 110 for enhanced radiographic visualization. In some embodiments, the elongate member 110 is at least partially a drawn-filled type of NiTi containing a different material at the core, such as a material with enhanced radiopacity, In some embodiments, the elongate member 110 has a radiopaque cladding or plating on at least portions of the elongate member 110. In some embodiments, one or more radiopaque markers are attached to the elongate member 110 (and/or to a covering material that is attached to the elongate member 110).

In some embodiments, the diameter or thickness of the elongate member 110 is within a range of about 0.1 mm to about 1.50 mm, but in some embodiments an elongate member 110 having smaller or larger diameters can be used. In some embodiments, the diameter of thickness of the elongate member 110 is within a range of about 0.2 mm to about 0.5 mm. Notwithstanding, it should be clear that the elongate member 110, and the elongate members of other anastomosis devices provided herein, can have any suitable size or diameter.

In some embodiments, the elongate member 110 has a consistent diameter along the length of the elongate member 110. in some embodiments, one or more portions of the elongate member 110 are diametrically tapered or otherwise inconsistent in diameter. In some embodiments, the elongate member 110 may be formed using a center-less grinding technique, such that the diameter of the wire varies along the length of the elongate member 110. The elongate member 110 may have a round cross-sectional shape or may have a cross-sectional shape that is not round, such as a rectangle or other polygon. Examples of other cross-sectional shapes that the elongate member 110 may have include a square, oval, rectangle, triangle, D-shape, trapezoid, or irregular cross-sectional shape formed by a braided or stranded construct. In some embodiments, the elongate member 110 may comprise a flat wire. In some embodiments, a combination of such various types of elongate member 110 are used in an anastomosis device. While in some embodiments the elongate member 110 of the device has a uniform cross-sectional shape and size, in some embodiments, some portions of the elongate member 110 have a different cross-sectional shape and/or size than other portions of the elongate member 110.

The elongate member 110 of the anastomosis devices provided herein may exhibit, for example, beneficial fatigue resistance and elastic properties. In some embodiments, the elongate member 110 allows the anastomosis devices to be elastically crushed, folded, and/or collapsed into a low-profile configuration for containment within a lumen for transcatheter or endoscopic/thoracoscopic delivery, and to self-expand to an operative size and configuration once positioned at a desired target site within a body and deployed from the lumen.

In some embodiments, the elongate member 110 may include one or more fixation elements (e.g., anchors, barbs, protrusions, atraumatic members, and/or penetrating members, and combinations thereof). In some embodiments, such fixation elements advantageously reduce or inhibit in situ migration of the anastomosis devices after deployment to a target site within a body.

Still referring to FIGS. 1A, 1B, and 2, in some embodiments the first and second apposition portions 120 and 140 include multiple features that are configured to contact a surface of a tissue, and to provide an apposition force to the tissue surface. For example, in the depicted embodiment the one or more features of the first and second apposition portions 120 and 140 include elongate wire loops 122 and 142 respectively (such wire loops may also be referred to herein as fingers or petals). While in this embodiment, the first and second apposition portions 120 and 140 each include six wire loops 122 and 142, in some embodiments more or fewer than six wire loops 122 and 142 are included. For example, in some embodiments one, two, three, four, five, seven, eight, nine, ten, eleven, twelve, or more than twelve wire loops 122 and 142 are included in the first and second apposition portions 120 and 140.

While in the depicted embodiment, the wire loops 122 and 142 of the first and second apposition portions 120 and 140 are generally ovular in shape, it should be understood that an ovular shape is not required. For example, in some embodiments some or all of the wire loops 122 and/or 142 can be circular, triangular, linear, rectangular, diamond-shaped, and the like, and combinations thereof. For example, in some embodiments some or all of the wire loops 122 and/or 142 can have a first linear portion that projects radially from the central portion 130 and that is contiguous with a second diamond-shaped portion at the free end of the wire loops 122 and/or 142. Other combinations and sub-combinations of shapes are also envisioned.

While in the depicted embodiment the shape and size of all of the individual wire loops 122 and 142 are generally uniform, it should be understood that such uniformity is not a requirement. For example, in some embodiments one or more of the wire loops 122 can be shaped or sized differently from one or more other wire loops 122 of the same anastomosis device. Similarly, in some embodiments one or more of the wire loops 142 can be shaped or sized differently from one or more other wire loops 142 of the same anastomosis device. Further, the size and/or shape of some or all of the wire loops 122 can be different from the size and/or shape of some or all of the wire loops 142.

In some embodiments, some or all of the individual wire loops 122 and 142 are configured to independently bear loads associated with tissue surface contact. That is, in some embodiments individual ones of the wire loops 122 and/or 142 can be independently deflected in accordance with the topography of the tissue surface without imparting a substantial force to any other ones of the wire loops 122 and/or 142. In some embodiments, this feature can allow each of the wire loops 122 and/or 142 to provide an appositional force even though the tissue surface topography is not planar. Hence, in some embodiments the first and second apposition portions 120 and 140, or portions thereof, are configured to be highly conformable to irregular tissue surfaces. In some embodiments, portions of some or all of the individual wire loops 122 and/or 142 may abut or overlap with adjacent wire loops 122 and/or 142. In some such embodiments, some movements of the wire loops 122 and/or 142 may induce forces on one or more adjacent wire loops 122 and/or 142.

The elongate member 110 also forms the generally cylindrical central portion 130 (also referred to herein as the helical portion or tunnel portion). In some embodiments, the elongate member 110 is configured such that the central portion 130 is comprised of one or more segments of a helix. The one or more segments of a helix, when combined together, form the generally cylindrical central portion 130. As will be described further below, a generally fluid impermeable covering material can be disposed on the central portion 130 in some embodiments. The diameter of the central portion 130 can be made in any size as desired in order to suit the intended use of the anastomosis device.

While in some embodiments the central portion 130 is generally cylindrical, such a shape is not required. In some embodiments, some or all of the central portion 130 may have a cross-sectional shape such as, but not limited to, an elliptical cross-section, a polygonal cross-section, and other shapes. In some embodiments, the diameter of the lumen 132 is uniform along its entire length. In some embodiments, the diameter of the lumen 132 varies along its length. For example, in some embodiments the central portion 130 defines a lumen 132 that is frustoconical, to provide one such example embodiment of a lumen 132 with an inconsistent diameter.

In some embodiments, the elongate member 110 comprises a single continuous member that is formed in a pattern to define the first apposition portion 120, the central portion 130, and the second apposition portion 140. For example, in the depicted embodiment the wind pattern of the elongate member 110 can be described as follows. First, the elongate member 110 forms an individual wire loop 122 of the first apposition portion 120. After forming the individual wire loop 122, the elongate member 110 traverses the central portion 130 along a helical path in a direction away from the first apposition portion 120 and toward the second apposition portion 140. After traversing the central portion 130 along the helical path, the elongate member 110 forms an individual wire loop 142 of the second apposition portion 140. After forming the individual wire loop 142, the elongate member 110 traverses the central portion 130 along a helical path in a direction away from the second apposition portion 140 and toward the first apposition portion 120. Then the pattern is repeated so as to form another wire loop 122 and another wire loop 142, and so on, until the entire first apposition portion 120, central portion 130, and second apposition portion 140 have been fully formed. In some embodiments of the anastomosis devices provided herein, the aforementioned wind pattern, or many other types of wind patterns, can be used to create the frames for the anastomosis devices.

As described above, in some embodiments the elongate member 110 is a single continuous element. Accordingly, the elongate member 110 includes two free ends or termini. In some embodiments, the two free ends of the elongate member 110 can be conjoined such that the elongate member 110 forms a closed wind pattern (i.e., a continuous loop). The free ends of the elongate member 110 can be joined together using a variety of techniques including, but not limited to bonding, welding (e.g., laser welding), gluing, using a sleeve coupling, and the like, and combinations thereof. In some embodiments, a butt joint is used to join the free ends of the elongate member 110. In some embodiments, other types of joints can be used to join the free ends of the elongate member 110, including but not limited to, an overlap joint, a twist joint, a crimp joint, and the like, and combinations thereof. The free ends can be conjoined prior to or after heat-setting (in those embodiments that use a heat-setting process). In some embodiments, the free ends are not conjoined.

Referring to FIG. 1B in particular, the frame 100 defines a longitudinal axis 102 through the center of the lumen 132. While in some embodiments the wire loops 122 of the first apposition portion 120 are generally parallel with the wire loops 142 of the second apposition portion 140, in some embodiments some or all of the wire loops 122 of the first apposition portion 120 and some or all of the wire loops 142 of the second apposition portion 140 are not parallel. For example, in some embodiments the distance between some or all of the free ends of the wire loops 122 and 142 is less than the distance between the wire loops 122 and 142 near the central portion 130. In some embodiments, such a configuration provides an increased level of apposition force at the outer radius of the frame 100 as compared to nearer to the central portion 130. In some embodiments, the increased level of apposition force at the outer radius of the frame 100 can, in turn, facilitate conformance by the frame 100 to a significantly non-planar and irregular tissue surface. In some embodiments, to increase the level of apposition force provided by the frame 100 further, the distance between the free ends of the wire loops 122 and 142 can be reduced to essentially zero. In some embodiments, to increase the apposition force provided by the frame 100 still further, the wire loops 122 and 142 can intersect or cross over each other.

When the frame 100 is in its contracted configuration, as shown in FIG. 1B, the central portion 130 has a longitudinal length 'x.' In the depicted embodiment, when the frame 100 is in its contracted configuration, essentially no space exists between adjacent helical portions of elongate member 110 that make up the central portion 130. In some embodiments, when the frame 100 is in its contracted configuration, some space exists between adjacent helical portions of elongate member 110 that make up the central portion 130.

The longitudinal length 'x' can be selected by adjusting various design features of the frame 100. In a first example, the cross-sectional size (e.g., diameter) of the elongate member 110 can affect the length 'x.' In general, the larger the diameter of the elongate member 110, the longer the longitudinal length 'x.' In a second example, having greater numbers of wire loops 122 and 142 also increases the longitudinal length 'x.' That is the case because having greater numbers of wire loops 122 and 142 results in correspondingly more helical portions of elongate member 110 in the central portion 130. In a third example, having space between one or more of the helical portions of elongate member 110 in the central portion 130 also increases the longitudinal length 'x.'

Figure 3A:
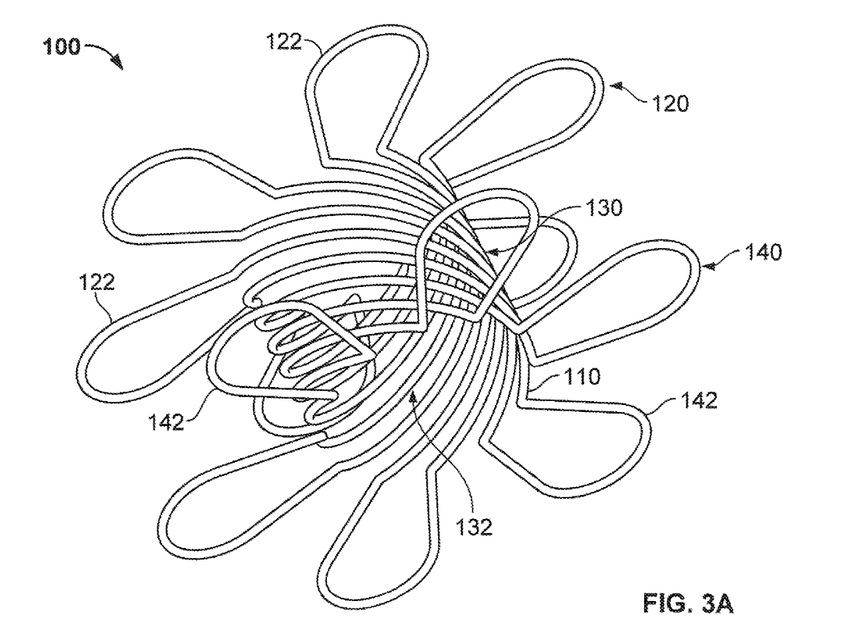
FIG. 3A is a perspective view of the wire frame of FIG. 1A in an extended configuration.
Figure 3B:
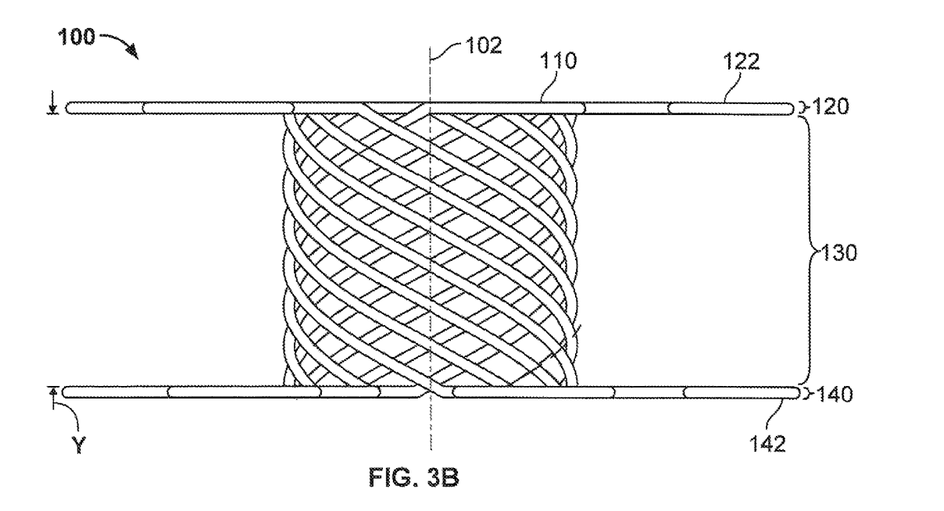
FIG. 3B is a side view of the wire frame of FIG. 1A in an extended configuration.

Referring now to FIGS. 3A and 3B, the frame 100 is shown in a longitudinally extended configuration (as compared to FIGS. 1A and 1B) such that the length of the central portion 130 has increased from distance 'x' to a longer distance 'y.' Such longitudinal extension of the depicted embodiment requires the application of a longitudinal tensile force to the frame 100. In other words, when the first and second apposition portions 120 and 140 are forced longitudinally away from each other the frame 100 is extended. The extension of the frame 100 results in the creation of spaces between the helical portions of elongate member 110 in the central portion 130. In some embodiments, the central portion 130 can be considered analogous to an extension spring. Therefore, in general the greater the distance 'y,' the greater the apposition forces delivered by the first and second apposition portions 120 and 140.

As the frame 100 is extended from its contracted configuration, the diameter of the lumen 132 changes comparatively little. That is the case because the helical portions of elongate member 110 in the central portion 130 are almost perpendicular to the longitudinal axis 102 when the frame 100 is in its contracted configuration. Therefore, as the frame 100 is extended, the resulting movements of the helical portions of elongate member 110 in the central portion 130 result in a substantially greater extension of the frame 100 than a diametrical reduction of the lumen 132. In some embodiments, such a capability of frame 100 to change in longitudinal length with little change in the lumen 132 diameter is advantageous for maintaining consistent patency of lumen 132 while accommodating variable tissue thicknesses.

Figure 4A:
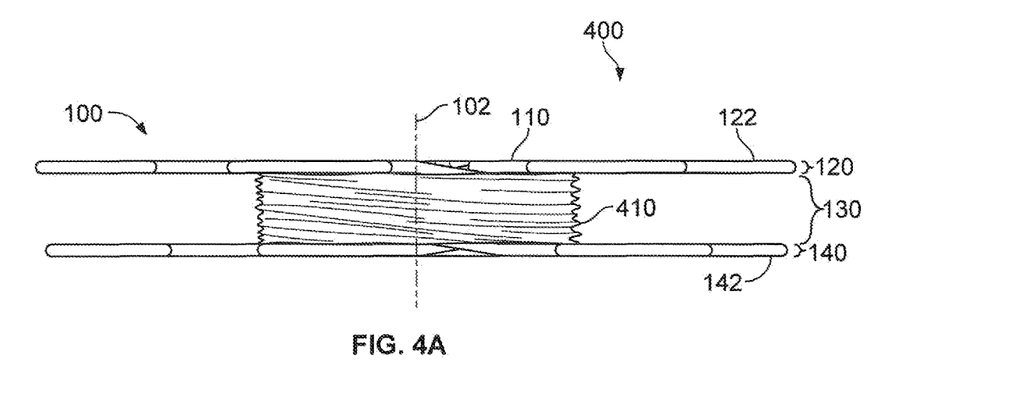
FIG. 4A is a side view of an example anastomosis device in a contracted configuration and including a covering material disposed on the central lumen portion of the anastomosis device.
Figure 4B:
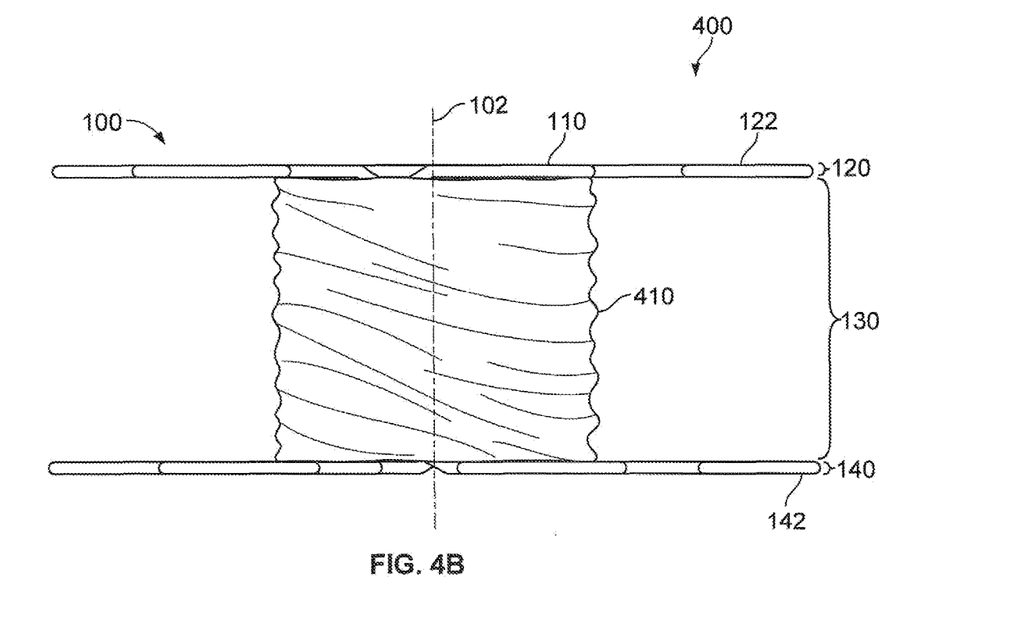
FIG. 4B is a side view of the anastomosis device of FIG. 4A in an extended configuration.

Referring now to FIGS. 4A-4B, an anastomosis device 400 includes the frame 100 and a covering material 210 (which may also be referred to herein as a sealing material). The covering material 210 can be disposed on and/or attached to one or more portions of the central portion 130 of the frame 100. In some embodiments, the covering material 210 can additionally, or alternatively, be disposed on one or both of the first and second apposition portions 120 and 140, or portions thereof.

In some embodiments, the covering material 210 is disposed on at least portions of the exterior of the central portion 130. In some embodiments, the covering material 210 is disposed on at least portions of the interior of the central portion 130. In some embodiments, the covering material is disposed on at least portions of both the interior and exterior of the central portion 130. The covering material 210 can, in some embodiments, enhance the tubular integrity of the lumen 132 (refer to FIGS. 1A-3B) so that the lumen 132 can function as an anastomosis conduit. Alternatively, the covering material 210 can be applied to the frame 100 so as to fully or partially occlude the lumen 132. In such cases, the resulting device can be used to seal an opening in a tissue (e.g., an aperture, puncture, tear, burst aneurysm, a resection area, and the like).

In some embodiments, the covering material 210 is made of a membranous material that inhibits or reduces passage of blood and/or other bodily fluids and materials through the covering material 210 itself. In some embodiments the covering material 210 has a material composition and configuration that inhibits or prevents tissue ingrowth and/or endothelialization into the covering material 210. Some such embodiments that are configured to inhibit or prevent tissue ingrowth and/or endothelialization can be more readily removed from the patient at a future date if so desired. In some embodiments, the covering material 210, or portions thereof, has a microporous structure that provides a tissue ingrowth scaffold for durable sealing and/or supplemental anchoring strength of the sealing device.

In some embodiments, the covering material 210 comprises a fluoropolymer, such as an expanded polytetrafluoroethylene (ePTFE) polymer. In some embodiments, the covering material 210 comprises a polyester, a silicone, a urethane, another biocompatible polymer, polyethylene terephthalate (e.g., Dacron®), bioabsorbable systems, copolymers, or combinations and subcombinations thereof.

In some embodiments, the covering material 210, or portions thereof, is modified by one or more chemical or physical processes that enhance one or more properties of the materials. For example, in some embodiments, a hydrophilic coating is applied to the covering material 210 to improve the wettability and echo translucency of the material 210. In some embodiments the covering material 210, or portions thereof, is modified with chemical moieties that facilitate one or more of endothelial cell attachment, endothelial cell migration, endothelial cell proliferation, and resistance to or promotion of thrombosis. In some embodiments the covering material 210, or portions thereof, is modified with one or more covalently attached drug substances (e.g., heparin, antibiotics, and the like) or impregnated with the one or more drug substances. The drug substances can be released in situ to promote healing, reduce tissue inflammation, reduce or inhibit infections, and to promote various other therapeutic treatments and outcomes. In some embodiments the drug substance is a corticosteroid, a human growth factor, an anti-mitotic agent, an antithrombotic agent, a stem cell material, or dexamethasone sodium phosphate, to name some examples. In some embodiments, a pharmacological agent is delivered separately from the covering material 210 to the target site to promote tissue healing or tissue growth.

Coatings and treatments may be applied to the covering material 210 before or after the covering material 210 is joined or disposed on the frame 100 of the anastomosis device 400. Additionally, one or both sides of the covering material 210, or portions thereof, may be coated. In some embodiments, certain coatings and/or treatments are applied to the material(s) located on some portions of the anastomosis device 400, and other coatings and/or treatments are applied to the material(s) located on other portions of the anastomosis device 400. In some embodiments, a combination of multiple coatings and/or treatments are applied to the covering material 210, or portions thereof. In some embodiments, certain portions of the covering material 210 are left uncoated and/or untreated.

In some embodiments, a first portion of the covering material 210 is formed of a first material and a second portion of the covering material 210 is formed of a second material. In some embodiments, the covering material 210 is comprised of multiple layers of materials, which may be the same or different materials, In some embodiments, portions of the covering material 210 have one or more radiopaque markers attached thereto to enhance in vivo radiographic visualization of the anastomosis device 400.

In some embodiments, one or more portions of the covering material 210 are attached to the elongate member 110, such as in the central portion 130. The attachment can be accomplished by a variety of techniques, such as by stitching the covering material 210 to the elongate member 110, by adhering the covering material 210 to the elongate member 110, by laminating multiple layers of the covering material 210 to encompass the elongate member 110, by using clips or barbs, or by other such techniques or combinations thereof. In some embodiments, the elongate member 110 of the frame 100, or portions thereof, may be coated with a bonding agent, for example fluorinated ethylene propylene (FEP) or other suitable adhesive for bonding the covering material 210 to the elongate member 110. The adhesive may be applied through contact coating, powder coating, dip coating, spray coating, or any other appropriate means. The frame 100 thereby provides a supportive structural framework for the covering material 210 that may be otherwise relatively flaccid.

In FIG. 4A, the frame 100 is depicted in its contracted configuration. In FIG. 46, the frame 100 is in an example extended configuration. The covering material 210 can adapt to such changing configurations of the frame 100, i.e., both the contracted and extended configurations. Additionally, as will be described further below, the covering material 210 can adapt to a low-profile delivery configuration in which the frame 100 is greatly elongated.

The covering material 210 can adapt to changes in the length and/or diameter of the central portion 130 in a variety of manners. In a first example, the covering material 210 can be elastic such that the covering material 210 can stretch to accommodate changes in the length and/or diameter of the central portion 130. In a second example, the covering material can include slackened material in the contracted configuration that becomes less slackened or totally unslacken as the central portion 130 is extended and/or enlarged. In a third example, the covering material 210 can include folding portions that are folded in the contracted configuration and less folded or totally unfolded as the central portion 130 is extended and/or enlarged. In some embodiments, combinations of such techniques, and/or other techniques can be used whereby the covering material 210 can adapt to changes in the length and/or diameter of the central portion 130.

As will be described further below, the configuration of the anastomosis device 400 (and other anastomosis device embodiments provided herein), as well as the flexibility and elasticity of the elongate member 110, make the anastomosis device 400 capable of transcatheter deployment. That is, in some embodiments the anastomosis device 400 can be elastically collapsed to a low-profile configuration for temporary containment within a lumen of a delivery catheter or sheath. To deploy the anastomosis device 400, the sheath containing the anastomosis device 400 in the low-profile configuration is inserted into the body of a patient and directed to a target site—typically using radiographic visualization (e.g., fluoroscopy), or using endoscopic optics for direct visualization. At the target site, the anastomosis device 400 is caused to emerge and become liberated from the sheath (e.g., using a pusher catheter), after which the anastomosis device 400 self-expands, or is caused to expand, to an enlarged configuration. For example, FIG. 1A shows the frame 100 of the anastomosis device 400 in the enlarged configuration that the frame 100 will naturally tend to seek in the absence of external constraining forces, such as those forces from a delivery sheath.

It should be understood that when the anastomosis device 400 is deployed in a patient's body, there will typically be constraining forces applied to the anastomosis device 400, such as from the tissue and the tissue aperture(s) in which the anastomosis device 400 resides. Because of those constraining forces, the shape of the anastomosis device 400 within the body may tend to be different than the shapes shown in the figures of the instant specification. Said another way, when the anastomosis device 400 is deployed within the body, the anastomosis device 400 will try to expand to its natural fully enlarged configuration, but the anastomosis device 400 may be constrained by the contours of the anatomy at the target site. In such circumstances, the shape of the anastomosis device 400 will tend to conform to the contours of the anatomy.

After the original deployment of the anastomosis device 400 at the target site, the contours of the anatomy may change over time. For example, if the anastomosis device 400 is deployed within the GI tract, the peristaltic wave motion of the intestines may change the contours of the anatomy at the target site. In that circumstance, the flexibility and elasticity of the anastomosis device 400 can allow the elongate member 110 to adapt in shape to facilitate resilient ongoing contact between the anastomosis device 400 and the surrounding tissue.

Referring now to FIGS. 5A-5E, an example anastomosis device system 500 can be used to deploy an example anastomosis device 530 to create a side-to-side anastomosis between two body conduits 540 and 550. The conduits 540 and 550 are shown in longitudinal cross-section to allow better visualization of the deployment of the anastomosis device 530 by the anastomosis device system 500. The conduits 540 and 550 may be intestines or blood vessels, for example. In some embodiments, the anastomosis device 530 is configured to be implanted such that a patent passageway or tunnel is created between the conduits 540 and 550. In some implementations, the anastomosis device 530 is implanted on a temporary basis while the tissues of the body conduits 540 and 550 grow together to form a tissue anastomosis, and thereafter the anastomosis device 530 is retrieved/removed from the implant site. In some implementations, the anastomosis device 530 is intended to remain implanted for a longer term or permanently.

The body conduits 540 and 550 can be prepared for the anastomosis by surgically closing the ends of the body conduits 540 and 550, and then connecting the closed end portions of the body conduits 540 and 550 in an overlapping arrangement. The anastomosis device system 500 can approach the overlapped portion of the body conduits 540 and 550 through one of the body conduits 540 or 550. For example, in some implementations the anastomosis device system 500 can approach the target implant site endoscopically.

The anastomosis device system 500 can include a sheath 510, an incision device 520, and the anastomosis device 530. The anastomosis device system 500 can be manipulated/operated externally of the patient's body by a clinician operator. In other words, the clinician operator can remotely operate the anastomosis device system 500 to perform the steps illustrated in FIGS. 5A-5E in a percutaneous fashion through an incision to the patient's skin, or through a natural patient orifice. In some implementations, fluoroscopy or other imaging modalities can be used during the deployment process to assist the clinician operator to implant the anastomosis device 530 in the target location as desired.

Figure 5A:
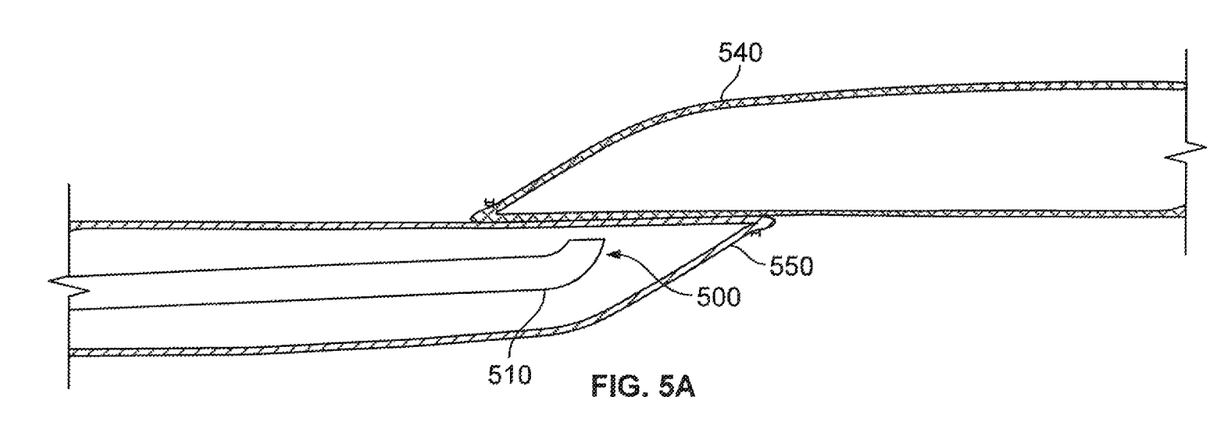
FIGS. 5A-5E are a series of illustrations depicting an example deployment process of an anastomosis device in accordance with some embodiments.

In FIG. 5A, the delivery sheath 510 approaches the target site through the body conduit 550. It should be understood that the anastomosis device 530 is positioned within a lumen of the sheath 510 during this step. Within the lumen, the anastomosis device 530 is configured in a low-profile configuration. To attain the low-profile configuration, the frame 100 (e.g., refer to FIG. 3B) can be elastically deflected and extended so that most portions of the elongate member 110 are substantially parallel with the longitudinal axis 102. In some cases, one or more portions of the anastomosis device 530 can be folded one or more times for containment within the sheath 510. In some embodiments, the sheath 510 has about a 15 Fr. (5 mm) outer diameter. However, in some embodiments, sheaths that are smaller or larger than 15 Fr. can be used. For example, sheaths that have outer diameters of 6 Fr., 7 Fr., 8 Fr., 9 Fr., 10 Fr., 11 Fr., 12 Fr., 13 Fr., 14 Fr., 16 Fr., 17 Fr., 18 Fr., 19 Fr., 20 Fr., and larger than 20 Fr., can be used in some embodiments.

Figure 5B:
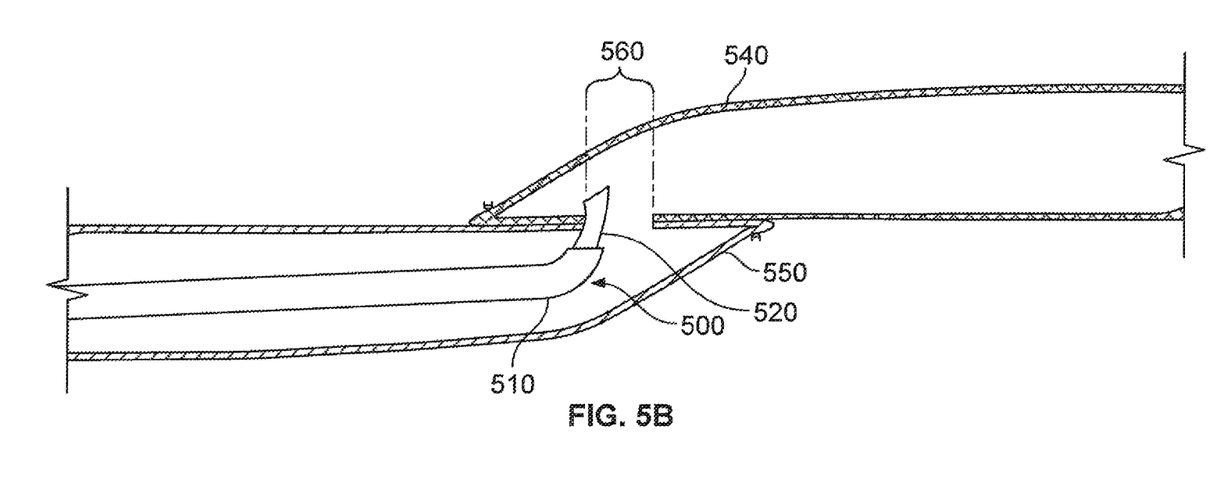

In FIG. 5B, the incision device 520 has been extended from the distal tip of the sheath 510, and the incision device 520 is being used to create an opening 560 through the walls of both body conduits 540 and 550. The incision device 520 can be a variety of different types of devices including, but not limited to, a scalpel, an electrocautery device, a surgical scissors, and the like. in some embodiments, the incision device 520 is separate from the sheath 510.

Figure 5C:
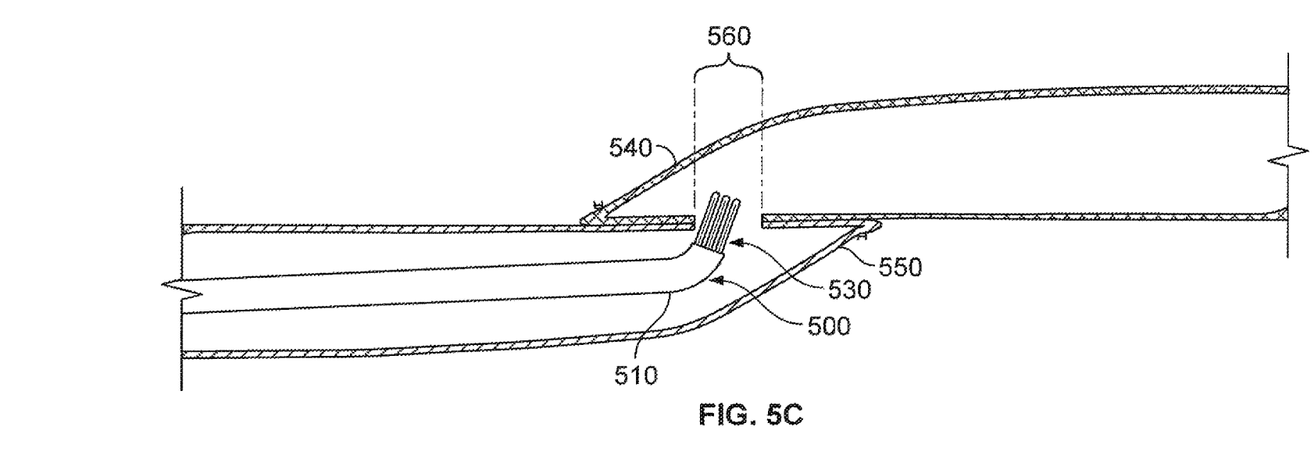

In FIG. 5C, the incision device 520 has been retracted, and the anastomosis device 530 is in the process of being expelled from the sheath 510 by the actions of the clinician operator. For example, in some embodiments, the clinician operator can expel the anastomosis device 530 from the sheath 510 by advancing a pusher catheter that is located within the sheath and that can push the anastomosis device 530 distally in relation to the sheath 510. During this step, the clinician operator positions the sheath 510 so that the leading portion of the anastomosis device 530 extends through the opening 560 and into the lumen of the body conduit 540. In some embodiments, one or more radiopaque markers are located on the anastomosis device 530 so that fluoroscopy can be used to assist the clinician to visually position the sheath 510 and/or the anastomosis device 530 as desired.

Figure 5D:
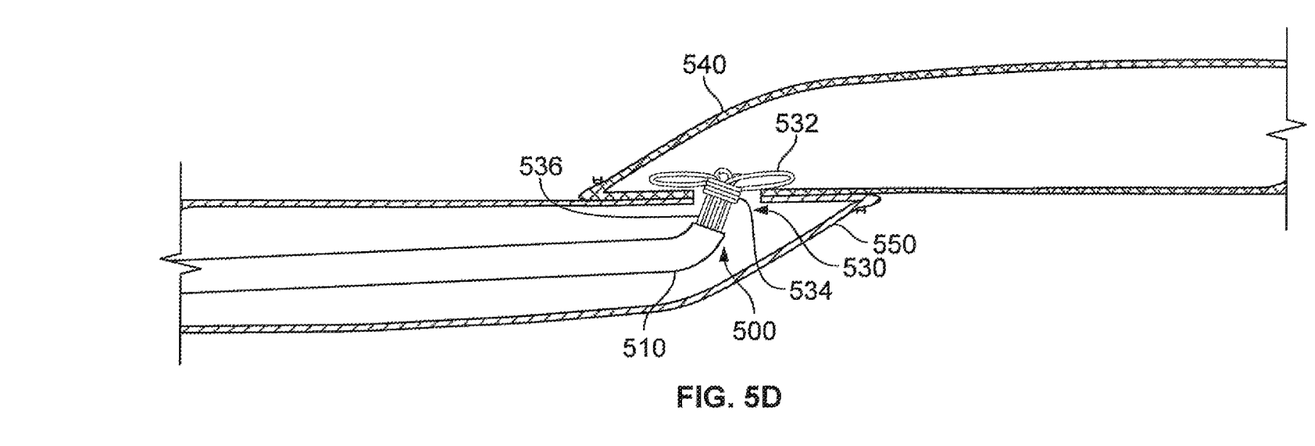

In FIG. 5D, the clinician operator has advanced the anastomosis device 530 such that a first apposition portion 532 and a central portion 534 of the anastomosis device 530 have emerged from the sheath 510. The first apposition portion 532 has expanded to form a generally circular disc. The central portion 534 has expanded to form a generally cylindrical shape with a lumen therethrough. The first apposition portion 532 is positioned in the body conduit 540. The central portion 534 is positioned in the opening 560.

Figure 5E:
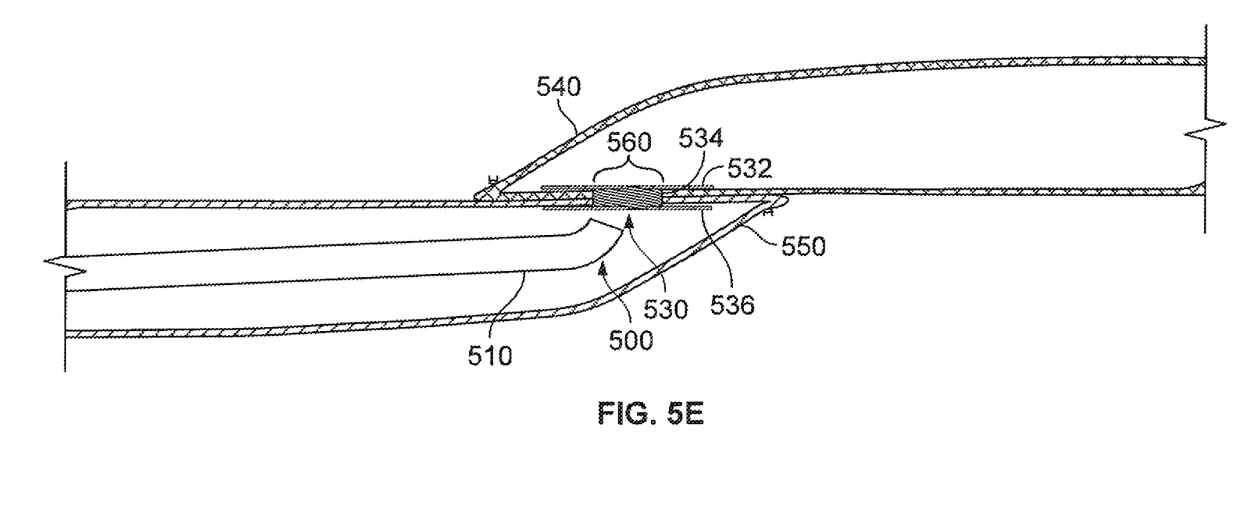

In FIG. 5E, the anastomosis device 530 has been fully deployed from the sheath 510 so as to create the anastomosis between the body conduits 540 and 550. The first apposition portion 532 is positioned in the body conduit 540. The second apposition portion 536 is positioned in the body conduit 550. The central portion 534 is positioned in the opening 560 between the first and second apposition portions 532 and 536. The first and second apposition portions 532 and 536 exert apposition forces to the respective tissue surfaces surrounding the opening 560. The central portion 534 maintains an open tunnel or passageway between the body conduits 540 and 550 to allow material flow therebetween.

In some embodiments, the anastomosis device 530 and other device embodiments provided herein are repositionable and/or retrievable after deployment. Therefore, if the initial deployment is deemed dissatisfactory, the anastomosis device 530 can be fully or partially retrieved into the sheath 510 and redeployed to a more desirable position.

The design of the anastomosis device 530 facilitates a durable patent anastomosis between the body conduits 540 and 550, notwithstanding the fact that some anatomical environments in which the anastomosis device 530 may be used are dynamic, such as the dynamic peristaltic motion environment of the GI tract. The anastomosis device 530 includes design features that facilitate resilient patency even in such dynamic environments. For example, the anastomosis device 530 is highly flexible and therefore highly conformable to irregular tissue topography and dynamic tissue topography. Furthermore, the apposition forces provided by the first apposition portion 532 and the second apposition portion 536 are substantially independent of the in situ device shape and/or diameter. In some embodiments, one or more auxiliary tissue anchorage features (e.g., anchors, barbs, protrusions, atraumatic members, and/or penetrating members, and combinations thereof) are included on the anastomosis device 530. Such anchorage features can provide increased fixation and to resistance to migration of the anastomosis device 530 within the body.

In some embodiments the anastomosis device 530 will be implanted in a patient for a temporary period of time. Anastomosis device 530 may be used, for example, to provide time to allow the tissues of the body conduits 540 and 550 to grow together to form a tissue anastomosis, and then the anastomosis device 530 can be removed. Therefore, in some such cases the anastomosis device 530 and other embodiments described herein can be deployed at the site of the anastomosis and later removed. In some embodiments, the anastomosis device 530, or portions thereof, are bioabsorbable such that some or all of the structure of the anastomosis device 530 will deteriorate in time. For example, in some such embodiments portions of the frame may deteriorate by bioabsorption, after which other portions of the anastomosis device 530 may be naturally expelled from the GI tract, or otherwise retrieved. In some cases, the elongate member may need to be severed in one or more locations prior to removal from the body. That may be the case, for example, when tissue growth has engulfed portions of the elongate member.

When retrieval of an anastomosis device, such as anastomosis device 530, from the body is desired, a retrieval sheath containing a grasping tool can be routed to the location of the anastomosis device in the patient's body. The grasping tool can be used to temporarily couple with the elongate member of the anastomosis device, such as a wire loop 122 or 142 of example frame 100. The grasping tool can then be retracted into the retrieval sheath. As the grasping tool is retracted into the retrieval sheath, the elongate member will begin to be drawn into the distal end of the retrieval sheath. In some embodiments, a funnel is included on the distal end portion of the retrieval sheath. The funnel will provide a wider initial opening at the distal tip of the retrieval sheath to facilitate the capture of all portions of the anastomosis device. As the grasping tool is further retracted, the entire anastomosis device can be pulled into the lumen of the retrieval sheath. Then the retrieval sheath, containing the anastomosis device, can then be removed from the patient.

In another example configuration of some embodiments of the anastomosis devices provided herein, the devices can be configured to occlude/seal a defect in the wall of a body lumen such as an intestine or blood vessel. In such a case, the anastomosis device includes a covering material that is arranged such that materials are inhibited or prevented from passing through the anastomosis device. The portion of the anastomosis device with the covering material is positioned on the inside of the body lumen. In that orientation, materials that are contained within the body lumen are occluded, i.e., prevented or inhibited from leaking from the body lumen. In addition, in that orientation the anastomosis device provides separation of intralumenal materials from the defect in the body lumen wall. The separation can, in some scenarios, allow healing of the defect, because contact of the biomaterials to the defect may tend to inhibit or prevent the healing process of the tissue surrounding the defect. For example, fecal matter within a colon would tend to inhibit the healing process of a perforation in the colon wall. In some such circumstances, the anastomosis device can be temporarily implanted in the body lumen such that the covering material overlays the perforation of the body lumen wall. After the perforation has healed and/or closed, the anastomosis device, or portions thereof, can be removed from the patient, or in some cases the anastomosis device, or portions thereof, may be naturally expelled by the body. While in some such implementations the anastomosis device is implanted temporarily, in some implementations the anastomosis device is implanted permanently.

Figure 6A:
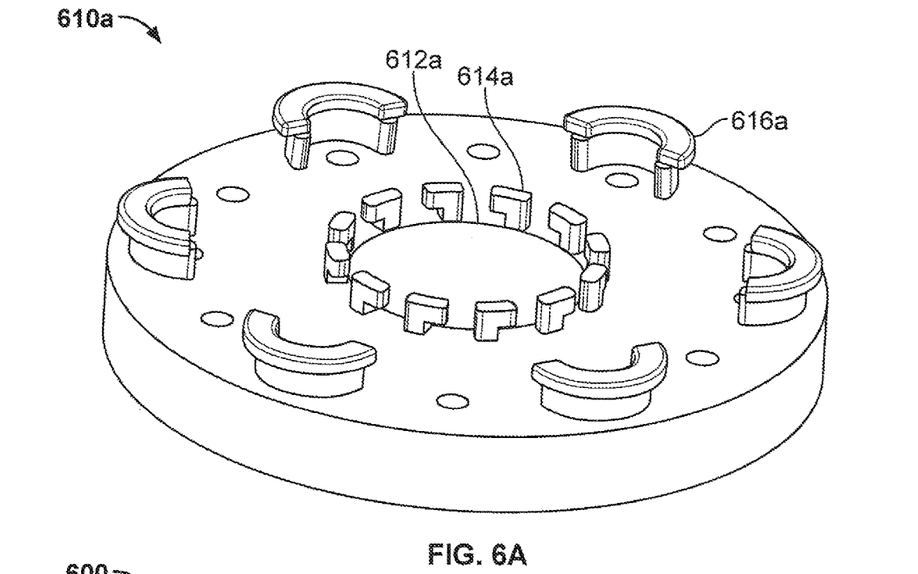
FIG. 6A is a perspective view of a portion of a wire winding mandrel that can be used to create the wire frame of FIG. 1A.
Figure 6B:
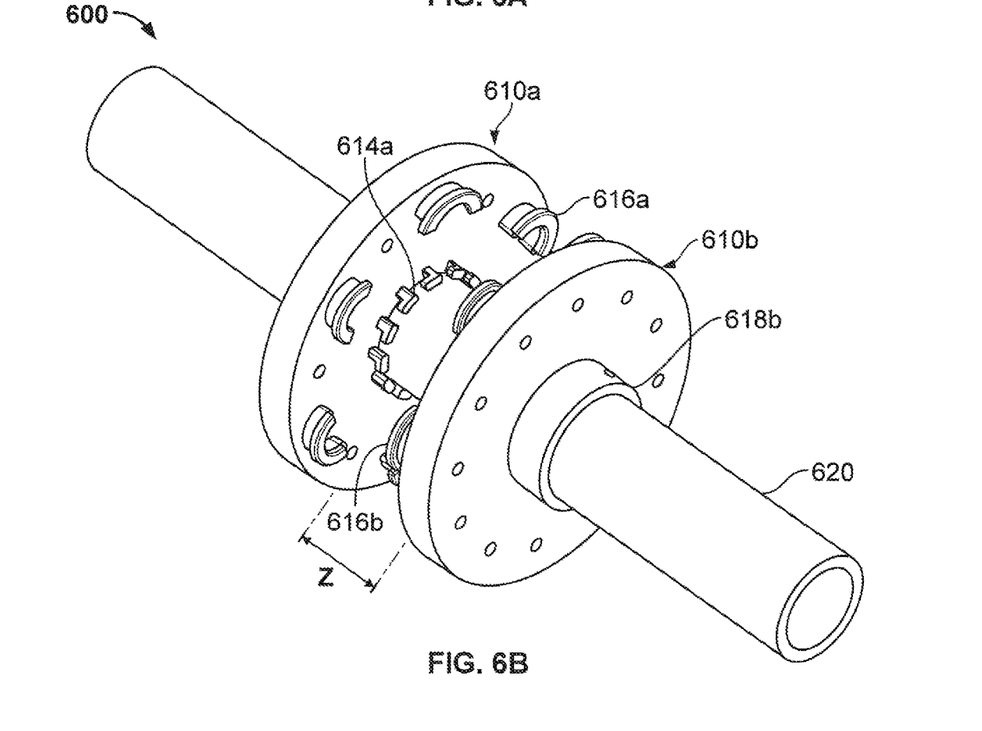
FIG. 6B is perspective view of a complete wire winding mandrel hat can be used to create the wire frame of FIG. 1A.

With reference to FIGS. 6A and 6B, an example wire winding mandrel 600 can be used to create some embodiments of the wire frames of the anastomosis devices provided herein. For example, the mandrel 600 can be used to create the frame 100 as shown in FIGS. 1A-3B. The winding mandrel 600 can be configured with the dimensional spacing, radii, and angles corresponding to the shape of the frame 100 as desired. The winding mandrel 600 can also be readily modified to create other embodiments of frames having other configurations as desired.

In some embodiments, the mandrel 600 includes two identical endplates 610*a-b* and a shaft 620. The endplates 610*a-b* are mounted onto the shaft 620 such that the endplates 610*a-b* are oriented in opposite directions of each other (like mirror images). Each endplate 610*a-b* includes a central bore 612*a-b* and a collar 618*a-b* which slidably receive the shaft 620. In some embodiments, the collar 618*a-b* includes a locking mechanism, such as a setscrew, by which the endplates 610*a-b* are releasably lockable to the shaft 620. When the individual locking mechanisms are released, the individual endplates 610*a* and/or 610*b* can be axially translated and/or rotated in relation to the shaft 620 and in relation to each other.

The endplates 610*a-b* include one or more inner hooks 614*a-b* and one or more outer arches 616*a-b*. In the depicted embodiment, the endplates 610*a-b* each include twelve inner hooks 614*a-b* and six outer arches 616*a-b*. Accordingly, the frame 100 that has six wire loops 122 and 142 can be formed using the depicted endplates 610*a-b*. In other embodiments of wire winding mandrel 600, fewer than six or more than six outer arches 616*a-b* can be included on each endplate 610*a-b*. Further, it should be understood that the outer arches 616*a-b* and inner hooks 614*a-b* can be configured with a variety of different geometries so that apposition features (e.g., wire loops 122 and 142) having the desired shape and size can be formed.

In some embodiments, to form the frame 100 an elongate member can be wound around a series of the inner hooks 614*a-b* and outer arches 616*a-b* in a pattern. During the winding, the endplates 610*a-b* are locked to the shaft 620 so that they are separated from each other by an example distance 'z.' In some embodiments, the winding pattern is as follows. First, the elongate member is engaged with a first inner hook 614*a* of endplate 610*a*. From the first inner hook 614*a*, the elongate member is wound around a first outer arch 616*a* of endplate 610*a* that is in general radial alignment with the first inner hook 614*a*. After winding the elongate member around the first outer arch 616*a*, the elongate member can be engaged with a second inner hook 614*a* of endplate 610*a* that is also in general radial alignment with the first outer arch 616*a*. From the second inner hook 614*a* of endplate 610*a*, the elongate member is routed toward the other endplate 610*b* along a path that is generally parallel to the shaft 620. At the endplate 610*b*, the elongate member is engaged with a first inner hook 612*b*. From the first inner hook 614*b*, the elongate member can be wound around a first outer arch 616*b* of endplate 610*b* that is in general radial alignment with the first inner hook 614*b*. After winding the elongate member around the first outer arch 616*b*, the elongate member can be engaged with a second inner hook 614*b* of endplate 610*b* that is also in general radial alignment with the first outer arch 616*b*. From there, the elongate member can be routed back toward the endplate 610*a* along a path that is generally parallel to the shaft 620. The pattern can then be repeated starting at a third inner hook 614*a*, and so on. In some embodiments, after the completion of the winding pattern, all inner hooks 614*a-b* and all outer arches 616*a-b* are in contact with the elongate member. The two free ends of the elongate member can then be secured either by conjoining the ends together, or by temporarily clamping them to the endplates 610*a-b*.

During the aforementioned process of winding the elongate member onto the wire winding mandrel 600, the endplates 610*a-b* are separated from each other by a distance 'z.' After that winding process, the central portion 130 of frame 100 is comprised of twelve linear portions of elongate member that are generally parallel to the shaft 620 and that have an approximate length of 'z.' Next, to continue the process of forming the frame 100, one of the endplates 610*a* or 610*b* is rotated and translated (simultaneously) in relation to shaft 620 while the other endplate 610a or 610b is maintained in a stationary position (e.g., locked) in relation to shaft 620. Naturally, as the endplates 610a-b are rotated in relation to each other, the elongate member portions in the central portion 130 will cause the endplates 610a-b to be drawn towards each other such that the separation will become less than distance 'z.' That relative motion between the endplates 610a and 610b will form the elongate member portions of the central portion 130 into segments of a helix as shown in FIGS. 1A-3B. The locking mechanisms of both endplates 610a-b are then activated to maintain the elongate member in the wound configuration.

In some embodiments, after the elongate member has been wound onto the winding mandrel 600 as described above, the assembly is heated to shape-set the elongate member to its as-wound shape. In one such non-limiting example, the elongate member is a NiTi wire, and the NiTi wire in a constrained state on the winding mandrel 600 is heated at about 470° C. for about 8 minutes. In other examples, higher or lower temperatures and shorter or longer times are used. The heating process will cause the NiTi wire to be heat-set into the wound shape or the memory shape. Accordingly, the NiTi wire will tend to naturally self-expand to reconfigure itself to the memory shape when deployed from a delivery sheath to a target site within a body.

While the example wire winding mandrel 600 is configured to create a frame 100 that has an angle between the first apposition portion 120 and the central portion 130 of about 90°, and an angle between the second apposition portion 140 and the central portion of about 90°, it should be understood that mandrel 600 can be readily configured to create frames with such angles that are less than or more than 90°. Such angles can be equal to each other or unequal to each other. Further, in some embodiments the length of the helically wound central portion 130 is controlled by the combination of the distance 'z' and the diameter of the elongate member. That is, to create a frame with a longer central portion 130, a longer distance 'z' and/or a larger elongate member diameter can be selected.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Particular embodiments of the subject matter described in this specification can be implemented so as to realize one or more of the following advantages. In some embodiments, the anastomosis devices provided herein are configured to be highly conformable to the topography of tissue surfaces. The high conformability of the anastomosis devices makes them well-suited, for example, for performing anastomoses in areas including, but not limited to, GI tract lumens. Further, the conformability of the anastomosis devices provide resilient fixation and consistent patency between anastomosed conduits, even when treating body conduits that are subject to anatomical movements, such as the peristaltic movements of the GI tract. The anastomosis devices are also configured to not inhibit such anatomical movements. The anastomosis devices can allow the transfer of materials through the lumen of the device from one body conduit to another. In some embodiments, portions of the anastomosis device include a covering material to enhance the sealing characteristics of the device, and to inhibit tissue ingrowth to facilitate later removal of the device. In some embodiments, the anastomosis devices provided herein are configured to treat a wide variety of differently-sized and shaped tissues while exerting low apposition forces to the tissue surfaces. Thus, a single device may offer physicians the ability to connect tissues of several different sizes and shapes. In some embodiments, the anastomosis devices provided herein are configured to provide a generally consistent lumen diameter that is essentially independent of the in situ length of the device. In some embodiments, the anastomosis devices provided herein can be deployed to a target location within a patient's body using, a minimally invasive transcatheter technique. In some embodiments, the transcatheter deployment can be performed endoscopically or laparoscopically. In some embodiments, the anastomosis devices provided herein are repositionable and/or retrievable after deployment.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. A medical device for creating an anastomosis between a first body conduit and a second body conduit, the device comprising:
    a continuous elongate member defining a frame, the frame comprising:
        a first apposition portion including a first looped feature, the first apposition portion configured to conform to a geometry of a first tissue surface of the first body conduit and to provide an apposition force against the first tissue surface;
        a second apposition portion including a second looped feature, the second apposition portion configured to conform to a geometry of a second tissue surface of the second body conduit and to provide an apposition force against the second tissue surface; and
        a central portion between the first apposition portion and the second apposition portion, wherein the elongate member traverses the central portion in a helical pattern having a first winding direction from the first apposition portion to the second apposition portion, and then from the second apposition portion to the first apposition portion such that the central portion is longitudinally extendable and such that the central portion defines a lumen therethrough, wherein traversal of the central portion by the elongate member is only in the helical pattern having the first winding direction; and
    a covering material disposed on at least a portion of the central portion, the covering material being configured to allow material flow through the lumen and between the first body conduit and the second body conduit, wherein said frame has a contracted configuration and an expanded configuration; and
wherein said central portion has a diameter.

2. The device of claim 1, wherein the elongate member is wound in a pattern where (1) the elongate member defines the first looped feature, (2) the elongate member traverses the central portion in the helical pattern having the first winding direction along a helical path, (3) the elongate member defines the second looped feature, and (4) the elongate member traverses the central portion in the helical pattern having the first winding direction along a helical path, and
wherein the elongate member repeats the pattern such that a plurality of first looped features and a plurality of second looped features is formed.

3. The device of claim 2, wherein the first apposition portion comprises said plurality of first looped features and wherein the second apposition portion comprises said plurality of second looped features.

4. The device of claim 2, wherein said plurality of first looped features are offset from said plurality of second looped features.

5. The device of claim 2, wherein the plurality of first looped features comprise first one or more elongate wire loops, and wherein each of the first one or more elongate wire loops is configured to bear a load associated with the first tissue surface without imparting a substantial force to any other first one or more elongate wire loops.

6. The device of claim 5, wherein the plurality of second looped features comprise second one or more elongate wire loops, and wherein each of the second one or more elongate wire loops is configured to bear a load associated with the second tissue surface without imparting a substantial force to any other second one or more elongate wire loops.

7. The device of claim 1, wherein the elongate member traverses the central portion in the helical pattern having the first winding direction such that portions of the elongate member comprise a segment of a helix.

8. The device of claim 1, wherein the continuous elongate member is a single elongate member.

9. The device of claim 8, wherein the single elongate member traverses the central portion in the helical pattern having the first winding direction along a path comprising a segment of a helix.

10. The device of claim 9, wherein as said frame is positioned in said expanded configuration, movements of said elongate member in said central portion result in a greater longitudinal extension of said frame than a reduction in said diameter.

11. The device of claim 8, wherein the single continuous elongate member is a single wire.

12. The device of claim 11, wherein the single wire comprises nitinol.

13. The device of claim 11, wherein the single wire has a defined length and has a variable thickness throughout said length.

14. The device of claim 1, wherein the elongate member comprises a nitinol wire.

15. The device of claim 1, wherein the covering material is configured to inhibit tissue ingrowth or endothelialization into the covering material.

16. The device of claim 1, further comprising one or more radiopaque markers disposed on the device.

17. The device of claim 1, wherein the frame further comprises one or more tissue anchorage features.

18. The device of claim 1, wherein the covering material is also disposed on at least a portion of the first apposition portion or the second apposition portion.

19. The device of claim 1, wherein the covering material comprises expanded polytetrafluoroethylene (ePTFE).

20. A medical device for creating an anastomosis between a first body conduit and a second body conduit, the device comprising:
a frame comprising an elongate member, the elongate member defining:
a first apposition portion including a first looped feature, the first apposition portion configured to conform to a geometry of a first tissue surface of the first body conduit and to provide an apposition force against the first tissue surface;
a second apposition portion including a second looped feature, the second apposition portion configured to conform to a geometry of a second tissue surface of the second body conduit and to provide an apposition force against the second tissue surface; and
a central portion disposed between the first apposition portion and the second apposition portion, wherein the elongate member traverses the central portion in a helical pattern from the first apposition portion to the second apposition portion and then from the second apposition portion to the first apposition portion such that the central portion is longitudinally extendable and such that the central portion defines a lumen therethrough; and
a covering material disposed on at least a portion of the central portion, the covering material being configured to allow material flow through the lumen and between the first body conduit and the second body conduit,
wherein the frame has a contracted configuration and an expanded configuration; and
wherein the central portion has a diameter, and wherein helical portions of the elongate member in the central portion are substantially perpendicular to a longitudinal axis of the frame when the frame is in the contracted configuration.

21. The device of claim 20, wherein the elongate member is a single wire.

22. The device of claim 21, wherein the single wire comprises nitinol.

23. A medical device for creating an anastomosis between a first body conduit and a second body conduit, the device comprising:
a frame comprising an elongate member, the elongate member defining:
a first apposition portion including a first looped feature, the first apposition portion configured to conform to a geometry of a first tissue surface of the first body conduit and to provide an apposition force against the first tissue surface;
a second apposition portion including a second looped feature, the second apposition portion configured to conform to a geometry of a second tissue surface of the second body conduit and to provide an apposition force against the second tissue surface; and
a central portion disposed between the first apposition portion and the second apposition portion, wherein the elongate member traverses the central portion in a helical pattern from the first apposition portion to the second apposition portion and then from the second apposition portion to the first apposition portion such that the central portion is longitudinally extendable and such that the central portion defines a lumen therethrough; and a covering material disposed on at least a portion of the central portion, the covering material being configured to allow material flow through the lumen and between the first body conduit and the second body conduit, wherein the frame has a contracted configuration and an expanded configuration; and wherein the central portion has a diameter, and wherein as the frame is positioned in the expanded configuration, movements of the elongate member in the central portion result in a greater longitudinal extension of the frame than a reduction in the diameter.

24. The device of claim 23, wherein the elongate member is a single wire.

25. The device of claim 24, wherein the single wire comprises nitinol.

* * * * *